(12) United States Patent
Codignola et al.

(10) Patent No.: US 6,521,786 B1
(45) Date of Patent: Feb. 18, 2003

(54) PROCESS FOR THE PRODUCTION OF AROMATIC ACIDS

(76) Inventors: Franco Codignola, Corso Lodi 59, 20159, Milan (IT); Antonio Moro, Viale Emilia 85-20093 Cologno Monzese, Milan (IT)

( * ) Notice: Subject to any disclaimer, the term of this patent is extended or adjusted under 35 U.S.C. 154(b) by 0 days.

(21) Appl. No.: 09/913,080

(22) PCT Filed: Mar. 24, 2000

(86) PCT No.: PCT/EP00/02755

§ 371 (c)(1),
(2), (4) Date: Aug. 8, 2001

(87) PCT Pub. No.: WO00/58257

PCT Pub. Date: Oct. 5, 2000

(30) Foreign Application Priority Data

Mar. 25, 1999 (IT) .......................................... MI98A0606

(51) Int. Cl.[7] .............................................. C07C 51/16
(52) U.S. Cl. ....................... 562/412; 562/413; 562/414; 562/416; 562/417; 562/480; 562/425
(58) Field of Search ................................ 562/414, 413, 562/412, 480, 485, 416, 417

(56) References Cited

U.S. PATENT DOCUMENTS 5,292,934 A * 3/1994 Sikkenga et al.
6,137,001 A * 10/2000 Broeker et al.

FOREIGN PATENT DOCUMENTS

WO    WO-97/30963    * 8/1997
WO    WO-98/29378    * 7/1998

* cited by examiner

*Primary Examiner*—Peter O'Sullivan
(74) *Attorney, Agent, or Firm*—Stephen M. Nipper; Frank J. Dykas; Robert L. Shaver

(57) ABSTRACT

A description is given here of a novel process for the production of monocarboxylic and polycarboxylic aromatic acids by the catalytic oxidation in homogeneous phase of aromatic compounds carrying at least one oxidizable substituent group attached directly to the carbon atom of the corresponding aromatic nucleus. The novel process according to the present invention comprises the steps of: a) catalytically oxidizing the corresponding aromatic precursors in liquid phase in the presence of gaseous oxygen; b) filtering the end product; c) recycling into the oxidation reactor at least part of the mother liquors resulting from the filtration stage, and is characterized by the fact that said steps from (a) to (c) are carried out in a closed and continuous cycle operating substantially under the same pressure and temperature conditions, preferably at 2–10 barg and 100–140° C.

16 Claims, 2 Drawing Sheets

PROCESS FOR THE PRODUCTION OF AROMATIC ACIDS

Figure 1:
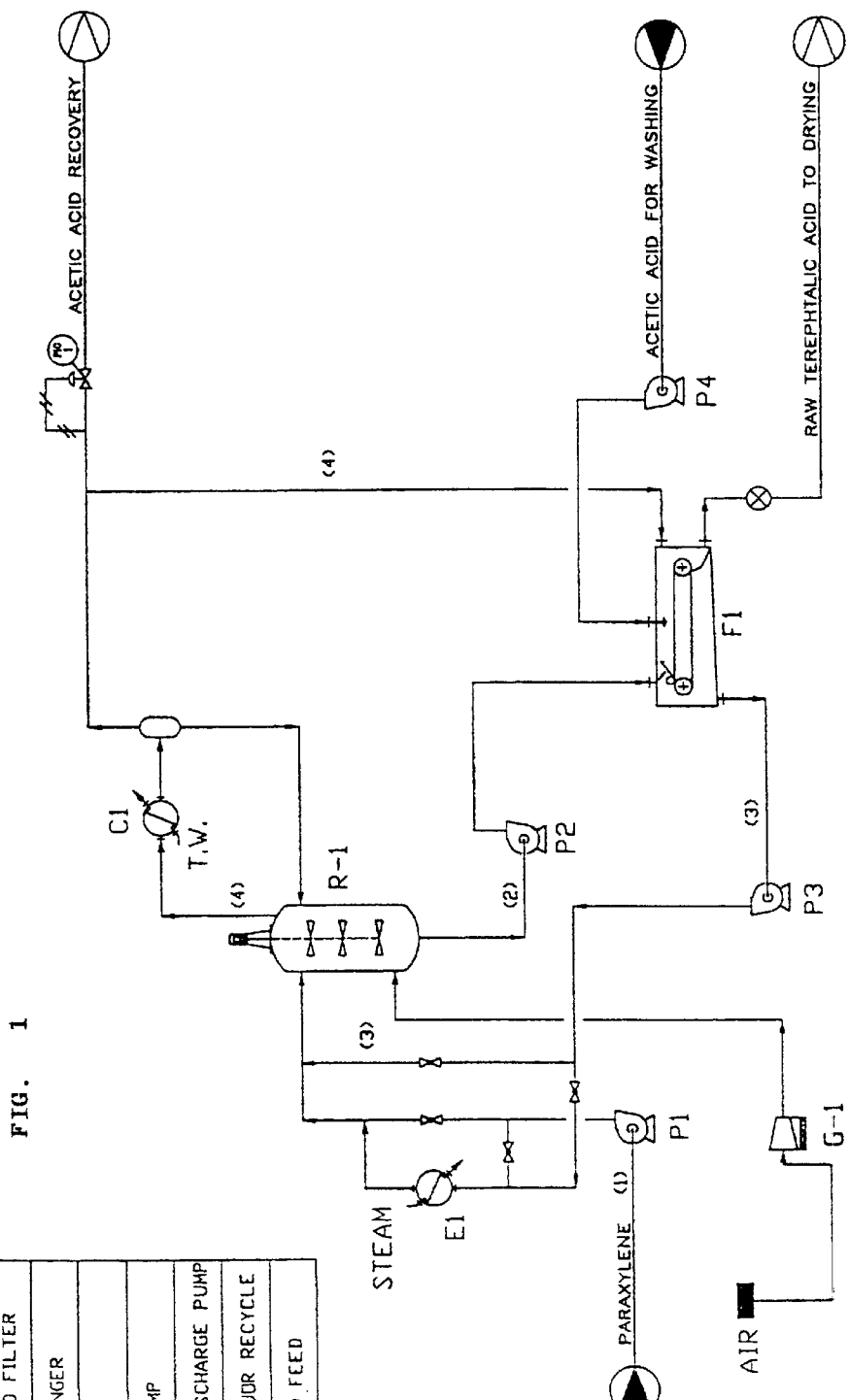

This application is a 371 of PCT/EP00/02755 filed Mar. 24, 2000.

The present invention relates to a novel process for the production of monocarboxylic and polycarboxylic aromatic acids by the catalytic oxidation in homogeneous phase of aromatic compounds carrying at least one oxidizable substituent group attached directly to the carbon atom of the corresponding aromatic nucleus.

FIELD OF THE INVENTION

Processes for the production of monocarboxylic and polycarboxylic aromatic acids are well known in the literature. They are normally carried out in liquid phase, operating either continuously or discontinuously and using as substrates aromatic compounds carrying at least one oxidisable substituent group attached directly to the carbon atom of the corresponding aromatic nucleus, where the expression "oxidisable substituent group" is intended to indicate any substituent in which a carbon atom is bonded directly to the aromatic nucleus and which, as a result of oxidation, is converted into a carboxylic group.

The oxidizing agent is generally gaseous molecular oxygen, preferably diluted with an inert gas; for obvious reasons of practicality air (optionally enriched with molecular oxygen) is the gaseous mixture most commonly used for this purpose. The oxidation reaction is normally carried out using as solvent an aqueous organic acid, preferably acetic acid, normally with a water content of from 2 to 5%.

Those reactions are carried out in the presence of a catalytic complex generally composed of one or more metals, normally in the form of salts soluble in the reaction solvent, and a suitable activator. The metal performs the function of catalyzing the actual oxidation reaction while the activator is used to return the metal (which undergoes a reduction in its oxidation number during catalysis) to its original valency, thus enabling it to regain and exert its catalytic activity. The activator may itself be a metal, in which case it also will preferably be present in the form of a salt soluble in the reaction medium; alternatively, it is possible to use organic compounds having carbonyl functions, such as ketones or aliphatic aldehydes, preferably acetaldehyde, or molecular bromine.

DE-1147571 discloses a method for the synthesis of phtalic acids by catalytic oxidation of the corresponding alkave precursors in liquid phase, the precursors are not dissolved in a suitable solvent but are used as the solvent themselves British patent GB-1063964 describes a process for the production of monocarboxylic and polycarboxylic aromatic acids at temperatures of preferably from 80 to 130° C. and pressures of from 1 to 60 $kg/cm^2$ by means of a catalytic complex substantially based on zirconium and cobalt.

U.S. Pat. No. 5,112,992 describes the production of aromatic acids at temperatures of from 100 to 275° C., using metals from groups IIIA and IVA of the periodic table of elements (groups IIIB and IVB according to the new notation adopted, for example, by Perry, *Chemical Engineers' Handbook*, VI edition, 1984), in particular zirconium and hafnium, in order to increase the kinetics of oxidation reactions that use catalytic complexes based on cobalt and manganese in the presence of bromine as the activator.

European patent application EP-475926 describes a process for the production of polycarboxylic aromatic acids which uses a catalytic complex based on manganese and cobalt and which operates at temperatures of from 100 to 220° C. and at pressures of 100 kilopascals or higher.

International patent application WO 98/29378 describes a catalytic complex, operating in absence of bromine, which comprises:

1. at least one metal having a valency higher than 2 which belongs to group VIIIA of the periodic table of elements, preferably ruthenium, iridium, palladium, platinum; and/or at least one metal from group VIIA, preferably rhenium; and/or cerium; and
2. at least one metal from group IVA of the periodic table of elements, preferably zirconium and/or hafnium;

where the catalytic pair cerium-zirconium constitutes the preferred complex for implementing the invention.

N.B. groups VIIIA, VIIA and IVA indicated above correspond, respectively, to groups VIII, VIIB and IVB according to the new notation adopted, for example, by Perry, *Chemical Engineers' Handbook*, VI edition.

The catalytic complex described in WO 98/29378 is used for the production of monocarboxylic and polycarboxylic aromatic acids, preferably from meta- and para-xylene, operating at temperatures of from 90 to 150° C., preferably from 105 to 115° C., and at pressures of from 1 to 20 barg, preferably from 2 to 5 barg.

Finally, U.S. Pat. No. 5,527,957, WO 93/24440, WO 97/30963 and WO 92/18454 disclose processes for the manufacture of polycarboxylic acids by catalytic oxidation in liquid phase of the corresponding precursors wherein the stage of filtering the end product is carried out at high pressures and temperatures whereas WO 96/111899 discloses a process for the manufacture of polycarboxylic acids in which the major portion of the mother liquors resulting from the filtration stage is recycled into the oxidation reactor.

The above listed five documents relate however to oxidation processes carried out in presence of bromine as the activator, whose activating action takes place at temperatures of about 150 to 250° C. and at pressures of at least 20–25 barg; given the high operating conditions, the corresponding plants have to be construed with particularly resistant materials, such as titanium or its alloys, with an evident increase in costs; a process for the manufacture of monocarboxylic and polycarboxylic aromatic acids in absence of bromine is thus preferable.

DESCRIPTION OF THE INVENTION

Monocarboxylic and polycarboxylic aromatic acids have a very low solubility in the solvents conventionally used in oxidation reactions of the type described above; therefore, they can be readily isolated from the reaction medium by simple filtration.

The catalytic complex used in the production of monocarboxylic and polycarboxylic acids is normally obtained by mixing into the reaction solvent at least one metal having catalytic action, generally in the form of a soluble salt, and an activator. The formation of the complex in its catalytically active state is not generally immediate but, depending on the case concerned, requires a time ranging from 30 to 90 minutes; this phenomenon is readily detectable with the naked eye because it is accompanied by a clear change in colour in the reaction solution.

The catalytic complex so formed is, however, a relatively unstable system; in fact, if it is not used within a short period, it undergoes a process of degradation which leads to a reduction in the valency of the metal which, in turn, loses its catalytic power; in this case too, the degradation of the catalytic complex is readily detectable with the naked eye because the solution containing it gradually returns to its original colour. In the mother liquors resulting from the production of monocarboxylic and polycarboxylic acids, this degradation process begins almost immediately after filtration and is generally complete within a few hours.

It will be appreciated that the degradation of the catalytic complex is a phenomenon which is hardly desirable because it involves not only a reduction in its oxidizing capacity (and therefore a drop in yield of the entire production cycle) but, much more seriously, a substantial reduction in its selectivity, with the consequent formation of mixtures of various products.

The object of the present invention is therefore to provide a novel process for the continuous production of monocarboxylic and/or polycarboxylic acids, such as, for example, benzoic acid, terephthalic acid, isophthalic acid, trimesic acid and N-2,6-naphthalenedicarboxylic acid, by the oxidation in liquid phase of the corresponding alkyl aromatic hydrocarbons in absence of bromine, which process does not have the disadvantages specified above; in particular, it relates to a process operating at temperature and pressure conditions lower than those of standard bromine-based processes and in which of the catalytic complex is recycled in the reaction vessel without any substantial decrease in activity and selectivity.

The novel process for the production of monocarboxylic and polycarboxylic acids, which constitutes the main subject matter of the present invention, comprises the steps of (a) catalytically oxidizing the corresponding aromatic precursors in liquid phase in the presence of gaseous oxygen; (b) filtering the end product; (c) recycling into the oxidation reactor at least part of the mother liquors resulting from the filtration stage; and it is characterized by the fact that said steps from (a) to (c) are carried out in a closed and continuous cycle operating substantially under the same pressure and temperature conditions.

According to a preferred embodiement of the invention, steps from (a) to (c) are maintained at the same pressure and temperature conditions by recycling at least some of the exhaust gases coming from the oxidation reaction. Preferably, the steps of (a) catalytically oxidizing the aromatic precursors in liquid phase in the presence of gaseous oxygen; (b) filtering the end product; (c) recycling into the oxidation reactor at least part of the mother liquors resulting from the filtration stage are carried out at a pressure of from 1 to 20 barg, preferably from 2 to 10 barg, and at a temperature of from 90 to 150° C., preferably from 100 to 140° C.

According to a further aspect of the invention, more than 50% by weight of the mother liquors resulting from the filtration stage are recycled into the oxidation reactor substantially under the same pressure and temperature conditions as the filtration stage; according to a preferred embodiment, from 60 to 100% by weight of the mother liquors resulting from the filtration stage are recycled into the oxidation reactor, even more preferably from 80 to 100%.

The mother liquors may be recycled directly into the oxidation reactor or they may be mixed beforehand with the solution containing the alkyl aromatic hydrocarbons which supplies the reactor. The process according to the present invention may be carried out in conjunction with the various catalytic complexes known in the art and, in general, with the catalytic complexes described WO 98/29378, which is to be regarded as included in the present description. The process can also be used in conjunction with catalytic complexes in which the metal is activated by carbonyl products or by another metal which, together therewith, forms an oxidation-reduction pair. The catalytic metals which may preferably be used are those of group VIII (Perry, *Chemical Engineers' Handbook*, VI edition) and cerium; the carbonyl activators are, however, preferably selected from acetaldehyde and its polymers and methyl ethyl ketone, while the metal activators are selected from zirconium and hafnium. According to the preferred embodiment of the present invention, the catalytic complex consists of a mixture of cobalt and zirconium salts or cerium and zirconium salts.

The reaction solvent is normally constituted by $C_1$–$C_6$ aliphatic acids or mixtures thereof, preferably acetic acid, which constitute from 75 to 80% by weight of the reaction mixture; the water content of those acids should preferably not exceed 4 to 12% by weight. On the other hand, the substrate of the oxidation reaction, or the alkyl aromatic hydrocarbons, normally constitutes from 15 to 20% by weight of the reaction mixture.

Filters which may preferably be used in the process of the present invention are so-called "pressure" filters, in this case also generally belt filters (Pannevis) or filters of the circular type, such as the Bird-Young Rotatory Filter produced by Bird. Filters of that type are usually maintained at the operating pressure by means of an additional stream of an inert gas. According to a further preferred aspect of the present invention, however, the stream of inert gas is replaced by at least some of the exhaust gases coming from the oxidation reactor, which are normally composed of the residual oxidation mixture and of secondary products of the oxidation reaction which thus contribute to maintaining the filter under the operating conditions described above. Before being sent to the filter, the above-mentioned exhaust gases may be subjected to an optional condensation stage.

The preferred embodiment of the present invention is represented in FIG. 1, which is not to be regarded as limiting and which, in this particular case, concerns the oxidation of para-xylene to form terephthalic acid. The process in question may of course be used in conjunction with other reactions or operating stages which are typical of the production of carboxylic acids and which will be evident to any person skilled in the art; in this connection, the purification reactions described, for example, in U.S. Pat. Nos. 4,126, 638 and 4,629,715 are mentioned by way of example.

On the basis of the illustration in the above-mentioned FIG. 1, the reaction mixture (1) comprising the solvent, the starting materials and the catalytic complex is passed through a heat exchanger E1, by means of which it reaches a temperature of from 90 to 150° C., preferably from 100 to 140° C., and it is then supplied to the reactor R1 until a pressure of from 1 to 20 barg is reached, preferably from 2 to 10; once the oxidation reaction has started, the supplying of the reaction mixture (1) to the reactor R1 is resumed without the mixture having to pass through the exchanger E1; at the same time, the recovery of the suspension (2) containing the reacted product is started, the suspension then being sent to the filter F1 which likewise operates at a pressure of from 1 to 20 barg, preferably from 2 to 10. The mother liquors (3) resulting from filtration are then recycled into the reactor R1 by means of pump P3 which maintains them substantially at the same pressure conditions of the filtration stage whereas it is usually not necessary for them to pass through the exchanger E1 in order to maintain the same temperature conditions. In the meantime, at least some of the exhaust gases (4) are recycled to the pressure filter F1 in order to maintain the whole cycle at the same operating pressure and temperature conditions; the amount of exhaust gases to be recycled cannot be normally foreseen as it will depend on the technical and structural characteristic of the plant.

The invention therefore relates also to an installation for the production of monocarboxylic and polycarboxylic aromatic acids by catalytic oxidation of the corresponding aromatic precursors in liquid phase in the presence of gaseous oxygen, which installation comprises an oxidation reactor and a filter arranged downstream of the oxidation reactor, in which:

a) both the oxidation reactor and the filter operate under the same pressure and temperature conditions;

b) more than 50% of the mother liquors resulting from the filtration stage are recycled into the oxidation reactor at the same pressure and temperature conditions of the oxidation and filtration stages; and in which c) at least some of the discharge gases coming from the oxidation reactor are supplied to the pressure filter.

The type of reactor is irrelevant to the implementation of the present invention and therefore the normal oxidation reactors known in the art may be used.

By means of the process and the installation according to the present invention, the process yield, expressed as kilograms of monocarboxylic and polycarboxylic aromatic acids per cubic meter of liquid phase of the reactor per year of oxidation, is substantially increased compared with classical processes which do not provide for the recycling of the major portion of the mother liquors at the same pressure and temperature conditions of the oxidation and filtration stage and the recycle of at least part of the exhaust gases.

It was also observed that there was a considerable increase in the selectivity of the oxidation catalyst which led to an almost total disappearance of any secondary oxidation products, thus making substantially superfluous any purification of the mother liquors of filtration before they are recycled into the oxidation reactor.

Finally, it has been observed that by maintaining both the liquid phase in the filter and the mother liquors resulting from the filtration stage are maintained in contact with at least part of the exhaust gases resulting from the oxidation stage, the degradation of the catalytic complex is substantially reduced, with advantages which will be evident to any skilled in this art.

Those and other aspects of the invention are indicated in the following Examples which are to be regarded as non-limiting illustrations of the invention.

EXAMPLE NO. 1

At start-up, there are charged into a reactor having a useful volume of 50 liters, 25 kg of a reaction mixture having the following composition by weight:

| | |
|---|---|
| para-xylene | 15% |
| glacial acetic acid | 80% |
| $H_2O$ | 5% |
| cobalt acetate tetrahydrate | 936 g |
| zirconium acetate | 90 g |

The temperature of the mixture is increased to 90° C. The injection of air is started, and then the temperature is increased until it reaches 110° C. and until a pressure of 8 barg is reached. After approximately 60 minutes, the colour of the reaction mixture becomes emerald green; after 310 minutes, the oxidation reaction is complete. At that point, the suspension of terephthalic acid starts to be supplied continuously to the filter, while, at the same time, para-xylene, the mother liquors, the acetic acid for washing the crude terephthalic acid so obtained and the make-up of the catalytic metals are supplied to the reactor.

Figure 2:
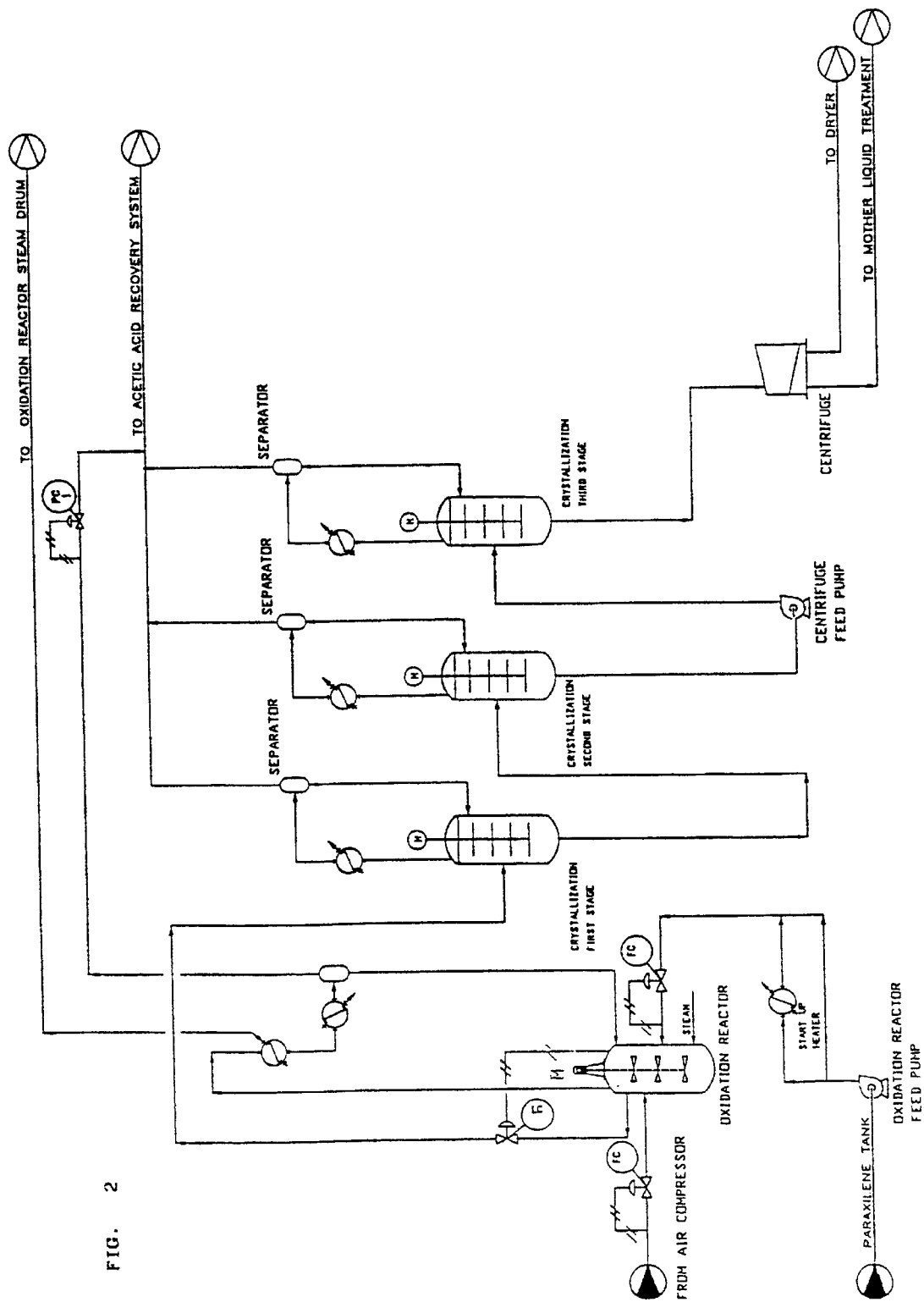

The oxidation process described above was carried out both in a pilot installation as described in FIG. 1, and in a conventional pilot installation having an open cycle (FIG. 2) which is provided with a filter operating at atmospheric pressure (centrifuge). In the case of the process according to FIG. 1, the mother liquors were maintained at a pressure of about 8 barg by means of pump P3; on the contrary, the temperature decrease was not relevant and it was therefore not necessary to use heat exchanger E1.

In the case of the novel process according to the present invention, the volumetric yield of the reactor was found to be 300 tonnes per cubic meter per year, in the case of the process that did not use a closed cycle, however, the yield per cubic meter fell to 240 tonnes per year.

EXAMPLE NO. 2

Substituting meta-xylene for the para-xylene of the previous Example, the volumetric yield per cubic meter was found to be 295 tonnes per year. The reduction is due to slightly lower kinetics and to the greater solubility of isophthalic acid which produces higher mechanical losses. As a result of not using the process with a closed cycle, the yield fell to 239 tonnes per cubic meter per year.

EXAMPLE NO. 3

The reaction mixture used for this Example has the following composition by weight:

| | |
|---|---|
| para-xylene | 15% |
| acetaldehyde | 15% |
| glacial acetic acid | 65% |
| $H_2O$ | 5% |
| cobalt acetate tetrahydrate | 475 g (on the total of the liquids) |

Using the closed-cycle process according to FIG. 1, the annual yield per cubic meter of reactor was found to be 295 tonnes. However, using a process according to FIG. 2, the yield falls to 225 tonnes per cubic meter per year.

What is claimed is:

1. A process for the production of monocarboxylic and/or polycarboxylic acids comprising the steps of (a) catalytically oxidizing the corresponding aromatic precursors in liquid phase in the presence of gaseous oxygen and of a catalytic complex consisting of a mixture of cobalt and zirconium salts or cerium and zirconium salts, in a reaction solvent constituted by $C_1$–$C_6$, aliphatic acids or mixtures thereof; (b) filtering the end product; (c) recycling into the oxidation reactor at least part of the mother liquors resulting from the filtration stage; said process being characterized in that said steps from (a) to (c) are carried out in a continuous cycle operating substantially under the same pressure and temperature conditions.

2. A process according to claim 1, characterized in that said $C_1$–$C_6$ aliphatic acid is acetic acid.

3. A process according to claim 2, characterized in that the acetic acid has a water content lower than 4% by weight.

4. A process according to claim 1, characterized in that said pressure and temperature conditions are maintained substantially unchanged in steps from (a) to (c) by recycling at least some of the exhaust gases coming from the oxidation reaction.

5. A process according to claim 1, characterized in that said steps from (a) to (c) are carried out at a pressure of from 1 to 20 barg and at a temperature of from 90 to 150° C.

6. A process according to claim 5, characterized in that said steps from (a) to (c) are carried out at a pressure of from 2 to 10 barg and at a temperature of from 100 to 140° C.

7. A process according to claim 1, characterized in that more than 50% by weight of the mother liquors resulting from the filtration stage are recycled into the oxidation reactor.

8. A process according to claim 7, characterized in that from 60 to 100% by weight of the mother liquors resulting from the filtration stage are recycled into the oxidation reactor.

9. A process according to claim 8, characterized in that all the mother liquors resulting from the filtration stage are recycled into the oxidation reactor.

10. A process according to claim 1, characterized in that both the liquid phase in the filter and the mother liquors resulting from the filtration stage are maintained in contact with at least part of the exhaust gases resulting from the oxidation stage.

11. A process according to claim 1, comprising the following steps: the reaction mixture (1) is passed through a heat exchanger E1 by means of which it reaches the temperature of from 90 to 150° C. and it is then supplied to the reactor R1 until the pressure of from 1 to 20 barg is reached; the reaction mixture (1) is then supplied to the reactor R1 without having to pass through the exchanger E1; the suspension (2) containing the reacted product is sent to the filter F1 while more than 50% by weight of the mother liquors (3) resulting from filtration are recycled into the reactor R1 at a pressure of from 1 to 20 barg without having to pass through the exchanger E1; at least some of the exhaust gases (4) are recycled to the filter F1.

12. A process according to claim 1, characterized by being carried out in absence of bromine.

13. A process according to claim 8, wherein said process is characterized in that from 80 to 100% by weight of the mother liquors resulting from the filtration stage are recycled into the oxidation reactor.

14. A process for the production of monocarboxylic and/or polycarboxylic acids comprising the steps of (a) catalytically oxidizing the corresponding aromatic precursors in liquid phase in the presence of gaseous oxygen and of a catalytic complex consisting of a mixture of cobalt and zirconium salts or cerium and zirconium salts, in a reaction solvent constituted by $C_1$–$C_6$, aliphatic acids or mixtures thereof; (b) filtering the end product; (c) recycling into the oxidation reactor at least part of the mother liquors resulting from the filtration stage; said process being characterized in that said steps from (a) to (c) are carried out in a continuous cycle operating substantially under the same pressure and temperature conditions; said process being characterized in that said pressure and temperature conditions are maintained substantially unchanged in steps from (a) to (c) by recycling at least some of the exhaust gases coming from the oxidation reaction.

15. A process for the production of monocarboxylic and/or polycarboxylic acids comprising the steps of (a) catalytically oxidizing the corresponding aromatic precursors in liquid phase in the presence of gaseous oxygen and of a catalytic complex consisting of a mixture of cobalt and zirconium salts or cerium and zirconium salts, in a reaction solvent constituted by $C_1$–$C_6$, aliphatic acids or mixtures thereof; (b) filtering the end product; (c) recycling into the oxidation reactor at least part of the mother liquors resulting from the filtration stage; said process being characterized in that said steps from (a) to (c) are carried out in a continuous cycle operating substantially under the same pressure and temperature conditions; said process being characterized in that both the liquid phase in the filter and the mother liquors resulting from the filtration stage are maintained in contact with at least part of the exhaust gases resulting from the oxidation stage.

16. A process for the production of monocarboxylic and/or polycarboxylic acids comprising the steps of (a) catalytically oxidizing the corresponding aromatic precursors in liquid phase in the presence of gaseous oxygen and of a catalytic complex consisting of a mixture of cobalt and zirconium salts or cerium and zirconium salts, in a reaction solvent constituted by $C_1$–$C_6$, aliphatic acids or mixtures thereof; (b) filtering the end product; (c) recycling into the oxidation reactor at least part of the mother liquors resulting from the filtration stage; said process being characterized in that said steps from (a) to (c) are carried out in a continuous cycle operating substantially under the same pressure and temperature conditions; said process further comprising the following steps; the reaction mixture (1) is passed through a heat exchanger E1 by means of which it reaches the temperature of from 90 to 150° C. and it is then supplied to the reactor R1 until the pressure of from 1 to 20 barg is reached; the reaction mixture (1) is then supplied to the reactor R1 without having to pass through the exchanger E1; the suspension (2) containing the reacted product is sent to the filter F1 while more than 50% by weight of the mother liquors (3) resulting from filtration are recycled into the reactor R1 at a pressure of from 1 to 20 barg without having to pass through the exchanger E1; at least some of the exhaust gases (4) are recycled to the filter F1.

* * * * *